(12) United States Patent
Schauer et al.

(10) Patent No.: US 12,029,890 B2
(45) Date of Patent: Jul. 9, 2024

(54) MAGNETIC DRIVES HAVING FLUX ENHANCERS FOR BLOOD PUMPS

(71) Applicant: Boston Scientific Scimed, Inc., Maple Grove, MN (US)

(72) Inventors: Travis J. Schauer, Rockford, MN (US); Joseph Alan Kronstedt, New Hope, MN (US); Benjamin Breidall, Eden Prairie, MN (US); Megan Johnson, Dayton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 333 days.

(21) Appl. No.: 17/137,175

(22) Filed: Dec. 29, 2020

(65) Prior Publication Data
US 2021/0220636 A1    Jul. 22, 2021

Related U.S. Application Data

(60) Provisional application No. 62/964,099, filed on Jan. 21, 2020.

(51) Int. Cl.
| | |
|---|---|
| *A61M 60/419* | (2021.01) |
| *A61M 60/13* | (2021.01) |
| *A61M 60/216* | (2021.01) |
| *A61M 60/221* | (2021.01) |
| *F04D 3/00* | (2006.01) |
| *F04D 13/02* | (2006.01) |

(52) U.S. Cl.
CPC .......... *A61M 60/419* (2021.01); *A61M 60/13* (2021.01); *A61M 60/216* (2021.01); *A61M 60/221* (2021.01); *F04D 3/005* (2013.01); *F04D 13/024* (2013.01); *F04D 13/027* (2013.01); *A61M 2205/0216* (2013.01)

(58) Field of Classification Search
CPC .. A61M 60/419; A61M 60/221; A61M 60/13; A61M 60/216; A61M 2205/0216; F04D 3/005; F04D 13/024; F04D 13/027
USPC ........................................................ 600/16
See application file for complete search history.

(56) References Cited

U.S. PATENT DOCUMENTS

| | | |
|---|---|---|
| 5,211,546 A | 5/1993 | Isaacson et al. |
| 5,507,629 A | 4/1996 | Jarvik |
| 5,527,159 A | 6/1996 | Bozeman, Jr. et al. |

(Continued)

FOREIGN PATENT DOCUMENTS

| | | |
|---|---|---|
| DE | 3338002 A1 | 5/1985 |
| JP | 04224760 A | 8/1992 |

(Continued)

OTHER PUBLICATIONS

International Search Report and Written Opinion received for PCT Patent Application No. PCT/US20/67375, dated Apr. 9, 2021, 15 pages.

(Continued)

*Primary Examiner* — Erin M Piateski
(74) *Attorney, Agent, or Firm* — Seager, Tufte & Wickhem LLP

(57) ABSTRACT

Various aspects of the present disclosure are directed to apparatuses, systems, and methods that may include a magnetic drive system of a blood pump. The magnetic drive system may include an impeller, a drive shaft, a driven magnet assembly, a driving magnet assembly, and a flux enhancer.

13 Claims, 4 Drawing Sheets

(56) References Cited

U.S. PATENT DOCUMENTS

| | | | |
|---|---|---|---|
| 5,611,679 A * | 3/1997 | Ghosh | F04D 13/027 417/420 |
| 5,928,131 A | 7/1999 | Prem | |
| 5,947,703 A | 9/1999 | Nojiri et al. | |
| 6,201,329 B1 | 3/2001 | Chen | |
| 6,227,820 B1 | 5/2001 | Jarvik | |
| 6,264,635 B1 | 7/2001 | Wampler et al. | |
| 6,447,266 B2 | 9/2002 | Antaki et al. | |
| 8,007,254 B2 | 8/2011 | Larose et al. | |
| 8,043,074 B2 | 10/2011 | Tada | |
| 8,512,012 B2 | 8/2013 | Akdis et al. | |
| 8,770,945 B2 | 7/2014 | Ozaki et al. | |
| 8,827,661 B2 | 9/2014 | Mori | |
| 9,067,005 B2 | 6/2015 | Ozaki et al. | |
| 9,091,271 B2 | 7/2015 | Bourque | |
| 9,199,020 B2 | 12/2015 | Siess | |
| 9,308,304 B2 | 4/2016 | Peters et al. | |
| 9,314,557 B2 | 4/2016 | Ricci et al. | |
| 9,364,594 B2 | 6/2016 | Nsser et al. | |
| 9,616,157 B2 | 4/2017 | Akdis | |
| 10,478,539 B2 | 11/2019 | Pfeffer et al. | |
| 10,704,553 B2 | 7/2020 | Janeczek et al. | |
| 10,780,208 B2 | 9/2020 | Siess et al. | |
| 10,842,921 B2 | 11/2020 | Siess et al. | |
| 10,894,115 B2 | 1/2021 | Pfeffer et al. | |
| 10,973,967 B2 | 4/2021 | Nyikos et al. | |
| 11,097,092 B2 | 8/2021 | Siess et al. | |
| 11,107,626 B2 | 8/2021 | Siess et al. | |
| 11,219,755 B2 | 1/2022 | Siess et al. | |
| 11,471,664 B2 | 10/2022 | Xu et al. | |
| 11,569,015 B2 | 1/2023 | Mourran et al. | |
| 11,648,388 B2 | 5/2023 | Siess et al. | |
| 11,672,968 B2 | 6/2023 | Antaki | |
| 2008/0085184 A1 * | 4/2008 | Wampler | A61M 60/824 415/170.1 |
| 2010/0135832 A1 * | 6/2010 | Wampler | A61M 60/422 417/423.1 |
| 2020/0306434 A1 | 10/2020 | Vancamp et al. | |
| 2021/0069393 A1 | 3/2021 | Schauer et al. | |
| 2022/0384070 A1 | 12/2022 | Mourran | |
| 2023/0040593 A1 | 2/2023 | Liu et al. | |

FOREIGN PATENT DOCUMENTS

| | | |
|---|---|---|
| JP | 05111535 A | 5/1993 |
| JP | 04224760 A | 8/1993 |
| JP | 2005094830 A | 4/2005 |
| JP | 2019150440 A | 9/2019 |
| WO | 95/00185 A1 | 1/1995 |
| WO | 9500185 A1 | 1/1995 |

OTHER PUBLICATIONS

International Search Report and Written Opinion for International Application No. PCT/US2020/067375, dated Apr. 9, 2021. (15 pages).

* cited by examiner

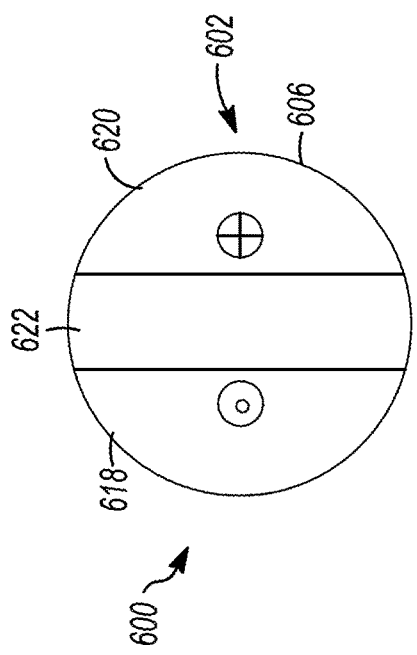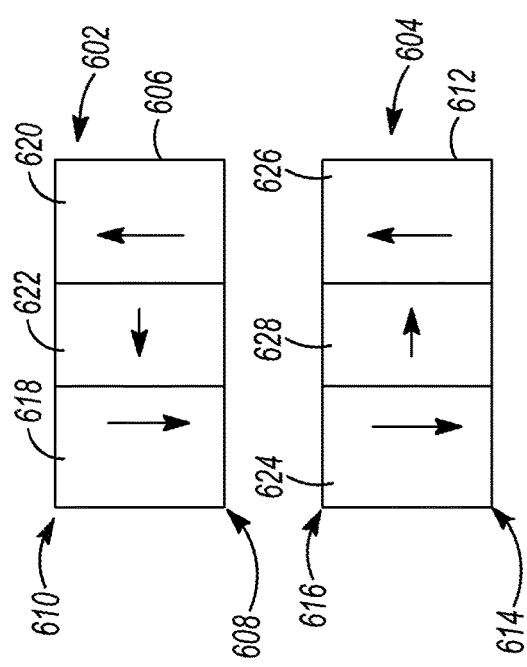

MAGNETIC DRIVES HAVING FLUX ENHANCERS FOR BLOOD PUMPS

CROSS REFERENCE TO RELATED APPLICATION

This application claims priority to Provisional Application No. 62/964,099, filed Jan. 21, 2020, which is herein incorporated by reference in its entirety.

TECHNICAL FIELD

The present disclosure relates to percutaneous circulatory support devices. More specifically, the disclosure relates to magnetic drives used in percutaneous circulatory support devices.

BACKGROUND

Percutaneous circulatory support devices such as blood pumps typically use motors to drive impeller assemblies to provide flow through the devices. Magnet assemblies may also be used in conjunction with such motors and assemblies to facilitate operation of the devices.

SUMMARY

In Example 1, a magnetic drive system of a blood pump, the magnetic drive system includes an impeller; a drive shaft; a driven magnet assembly; and a driving magnet assembly configured to drive the driven magnet assembly, at least one of the driven magnet assembly and the driving magnet assembly includes a flux enhancer.

In Example 2, the magnetic drive system of Example 1, the flux enhancer includes a soft magnetic material.

In Example 3, the magnetic drive system of Example 2, the driven magnet assembly includes a first flux enhancer and the driving magnet assembly includes a second flux enhancer.

In Example 4, the magnetic drive system of Example 3, the driven magnet assembly includes a first cylindrical body having a proximal end and a distal end; and the driving magnet assembly includes a second cylindrical body having a proximal end and a distal end.

In Example 5, the magnetic drive system of Example 4, the first cylindrical body includes a first section extending between the proximal and distal ends and having a circular segment cross section, a second section extending between the proximal and distal ends and having a circular segment cross section, and a third section disposed between the first and second sections and extending between the proximal and distal ends.

In Example 6, the magnetic drive system of either of Example 4 or 5, the first flux enhancer is disposed on the distal end of the first cylindrical body and covers at least a portion of the distal end of the first cylindrical body.

In Example 7, the magnetic drive system of Example 5, the third section of the first cylindrical body includes a first portion having a first end and a second end, the first end is disposed at the distal end of the first cylindrical body, and the first portion extends from the distal end to the second end; and a second portion having a first end and a second end, the first end is disposed adjacent the second end of the first portion, and the second portion extends from the first end to the proximal end of the first cylindrical body, the first portion of the third section of the first cylindrical body includes the first flux enhancer.

In Example 8, the magnetic drive system of Example 7, the second portion of the third section of the first cylindrical body has an axial length that is approximately two times longer than an axial length of the first portion of the third section.

In Example 9, the magnetic drive system of any of Examples 4-8, the second cylindrical body includes a first section extending between the proximal and distal ends and having a circular segment cross section, a second section extending between the proximal and distal ends and having a circular segment cross section, and a third section disposed between the first and second sections and extending between the proximal and distal ends.

In Example 10, the magnetic drive system of either of Example 4 or 9, the second flux enhancer is disposed on the proximal end of the second cylindrical body and covers at least a portion of the proximal end of the second cylindrical body.

In Example 11, the magnetic drive system of Example 9, the third section of the second cylindrical body includes a first portion having a first end and a second end, the first end is disposed at the proximal end of the second cylindrical body, and the first portion extends from the proximal end to the second end; and a second portion having a first end and a second end, the first end is disposed adjacent the second end of the first portion, and the second portion extends from the first end to the distal end of the second cylindrical body, the first portion of the third section of the second cylindrical body includes the second flux enhancer.

In Example 12, the magnetic drive system of Example 4, the driven magnet assembly further includes a third flux enhancer and the driving magnet assembly further includes a fourth flux enhancer, the first and third flux enhancers include sides irons disposed adjacent opposite magnetic poles on an outside of the first cylindrical body, and the second and fourth flux enhancers include side irons disposed adjacent opposite magnetic poles on an outside of the second cylindrical body.

In Example 13, the magnetic drive system of any of Examples 1-12, at least one of the driven magnet assembly and the driving magnet assembly includes two or more pole pairs.

In Example 14, a blood pump having a magnetic drive system, the magnetic drive system includes an impeller; a drive shaft; a driven magnet assembly; and a driving magnet assembly coupled to a motor and configured to drive the driven magnet assembly, at least one of the driven magnet assembly and the driving magnet assembly includes a flux enhancer.

In Example 15, the magnetic drive system of Example 14, the flux enhancer includes a soft magnetic material.

In Example 16, a magnetic drive system of a blood pump, the magnetic drive system includes an impeller; a drive shaft coupled to the impeller and configured to rotate with the impeller; a driven magnet assembly coupled to at least one of the drive shaft and the impeller; and a driving magnet assembly configured to drive the driven magnet assembly, at least one of the driven magnet assembly and the driving magnet assembly includes a flux enhancer.

In Example 17, the magnetic drive system of Example 16, the flux enhancer includes a soft magnetic material.

In Example 18, the magnetic drive system of Example 17, the driven magnet assembly includes a first flux enhancer and the driving magnet assembly includes a second flux enhancer.

In Example 19, the magnetic drive system of Example 18, the driven magnet assembly includes a first cylindrical body having a proximal end and a distal end; and the driving magnet assembly includes a second cylindrical body having a proximal end and a distal end.

In Example 20, the magnetic drive system of Example 19, the first cylindrical body includes a first section extending between the proximal and distal ends and having a circular segment cross section, a second section extending between the proximal and distal ends and having a circular segment cross section, and a third section disposed between the first and second sections and extending between the proximal and distal ends.

In Example 21, the magnetic drive system of Example 19, the first flux enhancer is disposed on the distal end of the first cylindrical body and covers at least a portion of the distal end of the first cylindrical body.

In Example 22, the magnetic drive system of Example 20, the third section of the first cylindrical body includes a first portion having a first end and a second end, the first end is disposed at the distal end of the first cylindrical body, and the first portion extends from the distal end to the second end; and a second portion having a first end and a second end, the first end is disposed adjacent the second end of the first portion, and the second portion extends from the first end to the proximal end of the first cylindrical body, the first portion of the third section of the first cylindrical body includes the first flux enhancer.

In Example 23, the magnetic drive system of Example 22, the second portion of the third section of the first cylindrical body has an axial length that is approximately two times longer than an axial length of the first portion of the third section.

In Example 24, the magnetic drive system of Example 19, the second cylindrical body includes a first section extending between the proximal and distal ends and having a circular segment cross section, a second section extending between the proximal and distal ends and having a circular segment cross section, and a third section disposed between the first and second sections and extending between the proximal and distal ends.

In Example 25, the magnetic drive system of Example 24, the second flux enhancer is disposed on the proximal end of the second cylindrical body and covers at least a portion of the proximal end of the second cylindrical body.

In Example 26, the magnetic drive system of Example 24, the third section of the second cylindrical body includes a first portion having a first end and a second end, the first end is disposed at the proximal end of the second cylindrical body, and the first portion extends from the proximal end to the second end; and a second portion having a first end and a second end, the first end is disposed adjacent the second end of the first portion, and the second portion extends from the first end to the distal end of the second cylindrical body, the first portion of the third section of the second cylindrical body includes the second flux enhancer.

In Example 27, the magnetic drive system of Example 19, the driven magnet assembly further includes a third flux enhancer and the driving magnet assembly further includes a fourth flux enhancer, the first and third flux enhancers include sides irons disposed adjacent opposite magnetic poles on an outside of the first cylindrical body, and the second and fourth flux enhancers include side irons disposed adjacent opposite magnetic poles on an outside of the second cylindrical body.

In Example 28, the magnetic drive system of Example 16, at least one of the driven magnet assembly and the driving magnet assembly includes two or more pole pairs.

In Example 29, a blood pump having a magnetic drive system, the magnetic drive system includes an impeller; a drive shaft coupled to the impeller and configured to rotate with the impeller; a driven magnet assembly coupled to at least one of the drive shaft and the impeller; and a driving magnet assembly coupled to a motor and configured to drive the driven magnet assembly, at least one of the driven magnet assembly and the driving magnet assembly includes a flux enhancer.

In Example 30, the blood pump of Example 29, the flux enhancer includes a soft magnetic material.

In Example 31, the blood pump of Example 30, the driven magnet assembly includes a first flux enhancer and the driving magnet assembly includes a second flux enhancer.

In Example 32, the blood pump of Example 31, the driven magnet assembly includes a first cylindrical body having a proximal end and a distal end; and the driving magnet assembly includes a second cylindrical body having a proximal end and a distal end.

In Example 33, the blood pump of Example 32, the first cylindrical body includes a first section extending between the proximal and distal ends and having a circular segment cross section, a second section extending between the proximal and distal ends and having a circular segment cross section, and a third section disposed between the first and second sections and extending between the proximal and distal ends.

In Example 34, the blood pump of Example 32, the first flux enhancer is disposed on the distal end of the first cylindrical body and covers at least a portion of the distal end of the first cylindrical body.

In Example 35, a blood pump having a magnetic drive system, the magnetic drive system includes an impeller; a drive shaft coupled to the impeller and configured to rotate with the impeller; a driven magnet assembly coupled to at least one of the drive shaft and the impeller; and a driving magnet assembly coupled to a motor and configured to drive the driven magnet assembly, the driven magnet assembly includes a first flux enhancer and the driving magnet assembly includes a second flux enhancer, the first and second flux enhancers each includes a soft magnetic material, and at least one of the driven magnet assembly and the driving magnet assembly includes two or more pole pairs.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIG. 6A depicts a top schematic view of an illustrative magnetic drive system, in accordance with embodiments of the subject matter disclosed herein.

FIG. 6B depicts a schematic side view of the magnetic drive system depicted in FIG. 6A, in accordance with embodiments of the subject matter disclosed herein.

Figure 1:
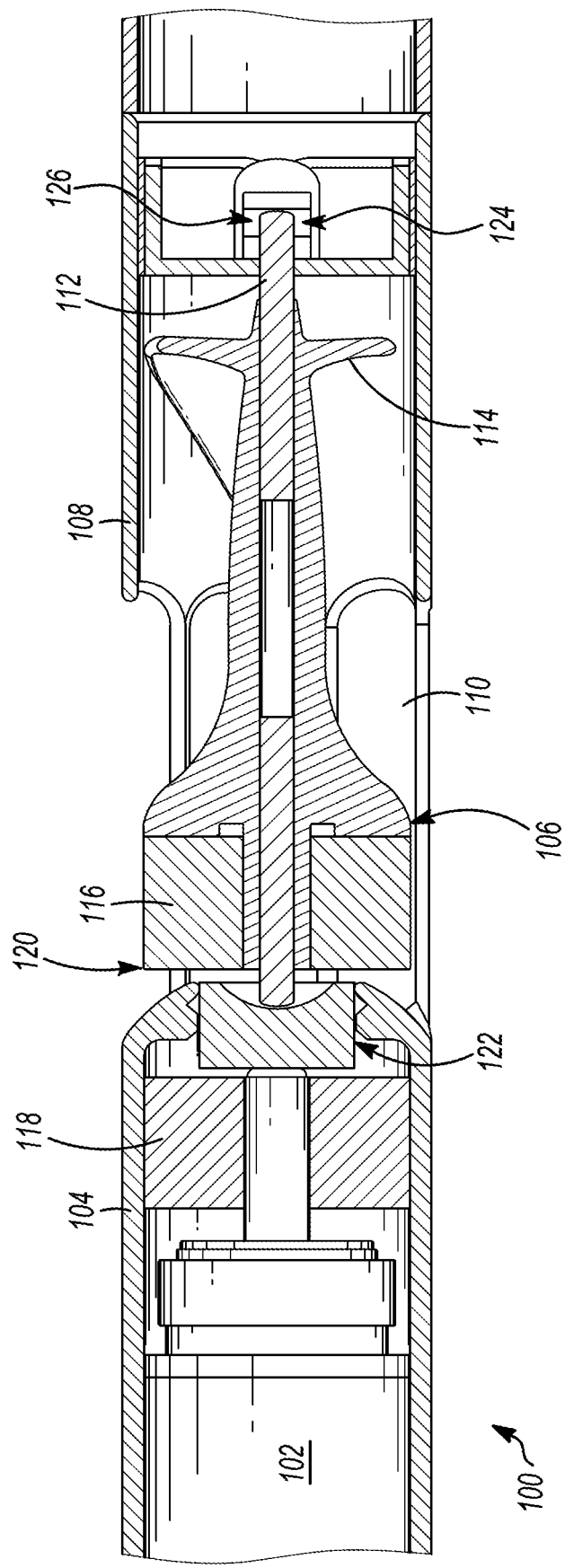
FIG. 1 depicts a cross-sectional side view of a portion of an illustrative percutaneous mechanical circulatory support device (also referred to herein, interchangeably, as a "blood pump"), in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

DETAILED DESCRIPTION

Embodiments of the subject matter disclosed herein include magnetic coupling designs that may facilitate efficient magnetic drive systems for circulatory support devices. According to embodiments, flux enhancers are used to focus magnetic fields to enhance magnetic coupling.

FIG. 1 depicts a cross-sectional side view of a portion of an illustrative percutaneous mechanical circulatory support device 100 (also referred to herein, interchangeably, as a "blood pump"), in accordance with embodiments of the subject matter disclosed herein. As shown in FIG. 1, the circulatory support device 100 includes a motor 102 disposed within a motor housing 104. The motor 102 is configured to drive an impeller assembly 106 to provide a flow of blood through the device 100. The impeller assembly 106 is disposed within an impeller assembly housing 108, which includes a number of outlet apertures 110 defined therein. According to embodiments, the motor housing 104 and the impeller assembly housing 108 may be integrated with one another. In other embodiments, the motor housing 104 and the impeller assembly housing 108 may be separate components configured to be coupled together, either removeably or permanently.

A controller (not shown) is operably coupled to the motor 102 and is configured to control the motor 102. The controller may be disposed within the motor housing 104 in embodiments, or in other embodiments, may be disposed outside the housing 104 (e.g., in a catheter handle, independent housing, etc.). In embodiments, the controller may include multiple components, one or more of which may be disposed within the housing 104. According to embodiments, the controller may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like.

As shown in FIG. 1, the impeller assembly 106 includes a drive shaft 112 and an impeller 114 coupled thereto, where the drive shaft 112 is configured to rotate with the impeller 114. As shown, the drive shaft 112 is at least partially disposed within the impeller 114. In embodiments, the drive shaft 112 may be made of any number of different rigid materials such as, for example, steel, titanium alloys, cobalt chromium alloys, nitinol, high-strength ceramics, and/or the like. The impeller assembly 106 further includes a driven magnet assembly 116 coupled to, and at least partially surrounding, the drive shaft 112. In embodiments, the driven magnet assembly 116 may be coupled to the drive shaft 112 and/or the impeller 114. The driven magnet assembly 116 may be any type of magnetic rotor capable of being driven by a driving magnet assembly 118 that is part of the motor 102. In this manner, as a magnetic field is applied to the driven magnet assembly 116 by the driving magnet assembly 118 in the motor 102, the driven magnet assembly 116 rotates, causing the drive shaft 112 and impeller 114 to rotate. In embodiments, the motor 102, drive shaft 112, impeller 114, driven magnet assembly 116, and driving magnet assembly 118 may be referred to as a magnetic drive system.

As described herein, at least one of the driven magnet assembly 116 and the driving magnet assembly 118 includes a flux enhancer. In embodiments, the driven magnet assembly 116 and/or the driving magnet assembly 118 may include more than one flux enhancer. Additionally, the driven magnet assembly 116 and/or the driving magnet assembly 118 may include more than one magnetic pole pair. The flux enhancer may include a soft magnetic material such as, for example, iron, iron-silicon alloys, nickel-iron alloys, and soft ferrites.

As shown, the impeller assembly 106 is maintained in its orientation by the drive shaft 112, which is retained at a first end 120 by a first bearing assembly 122 and at a second end 124 by a second bearing assembly 126. According to embodiments, the first bearing assembly 122 and the second bearing assembly 126 may include different types of bearings. According to embodiments, the first bearing assembly 122 and/or the second bearing assembly 126 may include lubrication, while in other embodiments, one and/or the other may not include lubrication.

The illustrative circulatory support device 100 shown in FIG. 1 is not intended to suggest any limitation as to the scope of use or functionality of embodiments of the present disclosure. The illustrative circulatory support device 100 also should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2A:
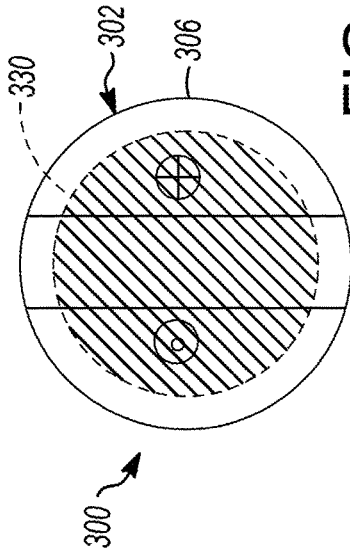
FIG. 2A depicts a top schematic view of an illustrative magnetic drive system, in accordance with embodiments of the subject matter disclosed herein.
Figure 2B:
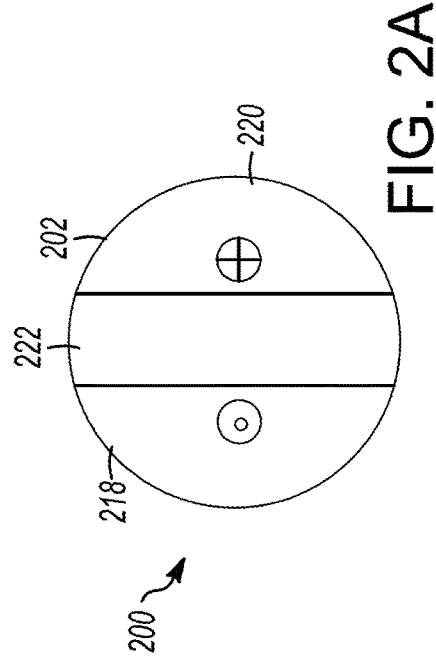
FIG. 2B depicts a schematic side view of the magnetic drive system depicted in FIG. 2A, in accordance with embodiments of the subject matter disclosed herein.

FIG. 2A depicts a top schematic view of an illustrative magnetic drive system 200, in accordance with embodiments of the subject matter disclosed herein; and FIG. 2B depicts a schematic side view of the magnetic drive system 200 depicted in FIG. 2A, in accordance with embodiments of the subject matter disclosed herein. According to embodiments, the magnetic drive system 200, and/or any number of various components thereof, may be the same as, or similar to, corresponding components of the circulatory support device 100 depicted in FIG. 1.

As shown in FIGS. 2A and 2B, the magnetic drive system 200 includes a driven magnet assembly 202 configured to be driven by a driving magnet assembly 204. According to embodiments, each of the driven magnet assembly 202 and the driving magnet assembly 204 may include any number of pole pairs (e.g., 1, 2, 3, 4, 5, 6, 7, 8, 9, etc.). The driven magnet assembly 202 includes a first cylindrical body 206 having a proximal end 208 and a distal end 210. Similarly, the driving magnet assembly 204 includes a second cylindrical body 212 having a proximal end 214 and a distal end 216.

The first cylindrical body 206 includes a first section 218 extending between the proximal and distal ends 208 and 210 and having a circular segment cross section, a second section 220 extending between the proximal and distal ends 208 and 210 and having a circular segment cross section, and a third section 222 disposed between the first and second sections 218 and 220 and extending between the proximal and distal ends 208 and 210. As shown, the first section 218 may include a permanent magnet having a magnetic field that is directed in the proximal direction, while the second section 220 may include a permanent magnet having a magnetic field that is directed in the distal direction.

As shown in FIG. 2B, the third section 222 of the first cylindrical body 206 includes a first portion 224 having a first end 226 and a second end 228, wherein the first end 226 is disposed at the distal end 210 of the first cylindrical body 206. The first portion 224 extends from the distal end 210 of the first cylindrical body 206 to the second end 228. The third section 222 of the first cylindrical body 206 also includes a second portion 230 having a first end 232 and a second end 234, wherein the first end 232 is disposed adjacent the second end 228 of the first portion 224. The second portion 230 extends from the first end 232 to the proximal end 208 of the first cylindrical body 206.

In embodiments, the first portion 224 of the third section 222 of the first cylindrical body 206 may be, or include, the first flux enhancer. For example, the first portion 224 may be a portion of soft magnetic material. The size (e.g., volume, length, and/or other dimensions) of the first portion 224 of the third section 222 of the first cylindrical body 206 may be designed to maximize magnetic flux therethrough to maximize, optimize, or otherwise facilitate magnetic coupling between the driven magnet assembly 202 and the driving magnet assembly 204. For example, in embodiments, second portion 230 of the third section 222 of the first cylindrical body 206 has an axial length 236 that is approximately two times longer than an axial length 238 of the first portion 224 of the third section 222. The second portion 230 of the third section 222 includes a non-magnetic material.

Similar to the driven magnet assembly 202, as indicated above, the driving magnet assembly 204 includes a second cylindrical body 212 having a proximal end 214 and a distal end 216. The second cylindrical body 212 includes a first section 240 extending between the proximal and distal ends 214 and 216 and having a circular segment cross section, a second section 242 extending between the proximal and distal ends 214 and 216 and having a circular segment cross section, and a third section 244 disposed between the first and second sections 240 and 242 and extending between the proximal and distal ends 214 and 216. As shown, the first section 240 may include a permanent magnet having a magnetic field that is directed in the proximal direction, while the second section 242 may include a permanent magnet having a magnetic field that is directed in the distal direction. In this manner, as the driving magnet assembly 204 rotates and each magnetic pole moves toward alignment with the opposite magnetic pole associated with a section of the driven magnet assembly 202, the driving magnet assembly 204 causes rotation of the driven magnet assembly 202.

As shown in FIG. 2B, the third section 244 of the second cylindrical body 212 includes a first portion 246 having a first end 248 and a second end 250, wherein the first end 248 is disposed at the proximal end 214 of the second cylindrical body 212. The first portion 246 extends from the proximal end 214 of the second cylindrical body 212 to the second end 250. The third section 244 of the second cylindrical body 212 also includes a second portion 252 having a first end 254 and a second end 256, wherein the first end 254 is disposed adjacent the second end 250 of the first portion 246. The second portion 252 extends from the first end 254 to the distal end 216 of the second cylindrical body 212.

In embodiments, the first portion 246 of the third section 244 of the second cylindrical body 212 may be, or include, a second flux enhancer. For example, the first portion 246 may be a portion of soft magnetic material. The size (e.g., volume, length, and/or other dimensions) of the first portion 246 of the third section 244 of the second cylindrical body 212 may be designed to maximize magnetic flux therethrough to maximize, optimize, or otherwise facilitate magnetic coupling between the driven magnet assembly 202 and the driving magnet assembly 204. For example, in embodiments, first and second portions 246 and 252 of the third section 244 of the second cylindrical body 212 may have the same, or similar, length ratio as the corresponding parts of the first cylindrical body 206. The second portion 252 of the third section 244 includes a non-magnetic material.

According to embodiments, as indicated above, the driven magnet assembly 202 and/or the driving magnet assembly 204 may include more than one pole pair. That is, for example, each cylindrical body may include a number of sections, each pair of sections having opposite magnetic poles and a flux enhancer disposed between them. In embodiments, then, each section may have a cross-section that is a different shape than a circular segment, such as, for example, a pie-piece shape. In some embodiments, each section may be cylindrical. To facilitate manufacturing, in embodiments, a cylindrical body of a magnet assembly may be made from non-magnetic material and may include chambers defined therein into which magnets are placed. Flux enhancers (portions of soft magnetic material) may be placed into other chambers, disposed between adjacent pairs of magnet chambers.

The illustrative magnetic drive system 200 shown in FIGS. 2A and 2B is not intended to suggest any limitation as to the scope of use or functionality of embodiments of the present disclosure. The illustrative magnetic drive system 200 also should not be interpreted as having any dependency or requirement related to any single component or combination of components illustrated therein. Additionally, various components depicted in FIGS. 2A and 2B may be, in embodiments, integrated with various ones of the other components depicted therein (and/or components not illustrated), all of which are considered to be within the ambit of the present disclosure.

Figure 3A:
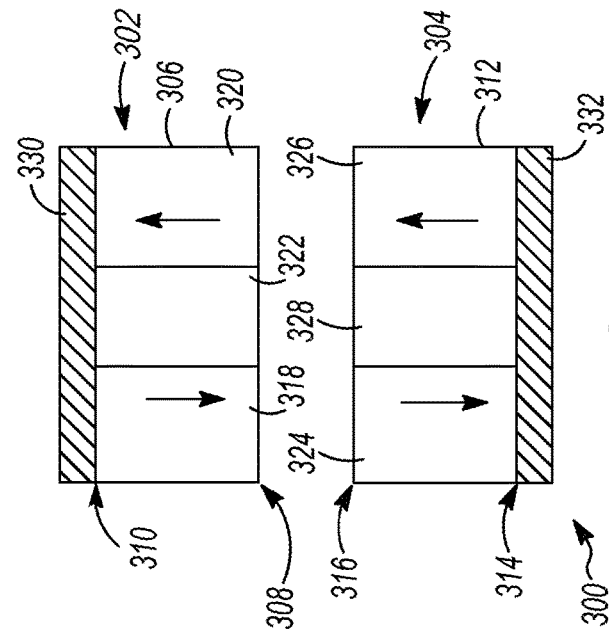
FIG. 3A depicts a top schematic view of an illustrative magnetic drive system, in accordance with embodiments of the subject matter disclosed herein.
Figure 3B:
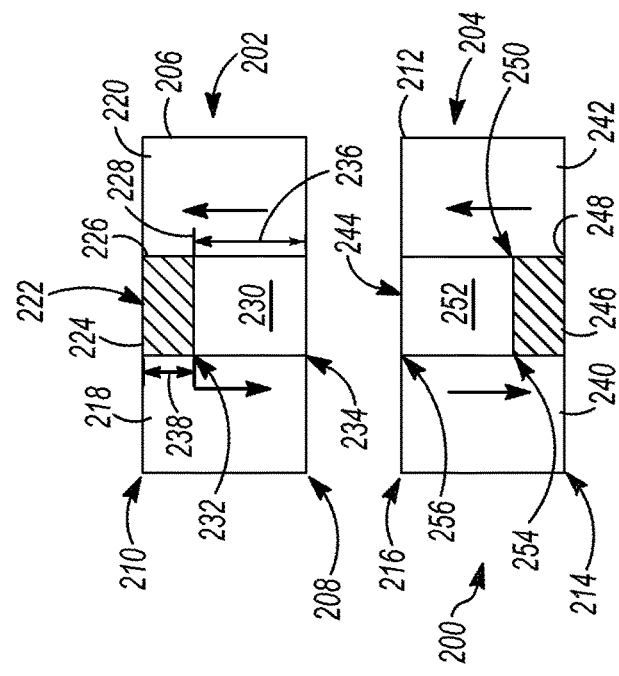
FIG. 3B depicts a schematic side view of the magnetic drive system depicted in FIG. 3A, in accordance with embodiments of the subject matter disclosed herein.

In embodiments, the flux enhancers may be disposed on ends of the cylindrical bodies. FIG. 3A depicts a top schematic view of an illustrative magnetic drive system 300, in accordance with embodiments of the subject matter disclosed herein; and FIG. 3B depicts a schematic side view of the magnetic drive system 300 depicted in FIG. 3A, in accordance with embodiments of the subject matter disclosed herein. According to embodiments, the magnetic drive system 300, and/or any number of various components thereof, may be the same as, or similar to, corresponding components of the circulatory support device 100 depicted in FIG. 1.

As shown in FIGS. 3A and 3B, the magnetic drive system 300 includes a driven magnet assembly 302 configured to be driven by a driving magnet assembly 304. According to embodiments, each of the driven magnet assembly 302 and the driving magnet assembly 304 may include any number of pole pairs (e.g., 1, 2, 3, 4, 5, 6, 7, 8, 9, 10, etc.). The driven magnet assembly 302 includes a first cylindrical body 306 having a proximal end 308 and a distal end 310. Similarly, the driving magnet assembly 304 includes a second cylindrical body 312 having a proximal end 314 and a distal end 316.

The first cylindrical body 306 includes a first section 318 extending between the proximal and distal ends 308 and 310 and having a circular segment cross section, a second section 320 extending between the proximal and distal ends 308 and 310 and having a circular segment cross section, and a third section 322 disposed between the first and second sections 318 and 320 and extending between the proximal and distal ends 308 and 310. As shown, the first section 318 may include a permanent magnet having a magnetic field that is directed in the proximal direction, while the second section 320 may include a permanent magnet having a magnetic field that is directed in the distal direction. The third section 322 may be formed from a non-magnetic material.

Similarly, the second cylindrical body 312 includes a first section 324 extending between the proximal and distal ends 314 and 316 and having a circular segment cross section, a second section 326 extending between the proximal and distal ends 314 and 316 and having a circular segment cross section, and a third section 328 disposed between the first and second sections 324 and 326 and extending between the proximal and distal ends 314 and 316. As shown, the first section 324 may include a permanent magnet having a magnetic field that is directed in the proximal direction, while the second section 326 may include a permanent magnet having a magnetic field that is directed in the distal direction. The third section 328 may be formed from a non-magnetic material.

A first flux enhancer 330 is disposed on the distal end 310 of the first cylindrical body 306 and covers at least a portion of the distal end 310 of the first cylindrical body 306. Similarly, a second flux enhancer 332 may be disposed on the proximal end 314 of the second cylindrical body 312 and may cover at least a portion of the proximal end 314 of the second cylindrical body 312. The flux enhancers 330 and 332 may be, for example, discs made from soft magnetic material.

According to embodiments, as indicated above, the driven magnet assembly 302 and/or the driving magnet assembly 304 may include more than one pole pair. That is, for example, each cylindrical body may include a number of sections, each pair of sections having opposite magnetic poles and a non-magnetic material disposed between them. In embodiments, then, each section may have a cross-section that is a different shape than a circular segment, such as, for example, a pie-piece shape. In some embodiments, each section may be cylindrical. To facilitate manufacturing, in embodiments, a cylindrical body of a magnet assembly may be made from non-magnetic material and may include chambers defined therein into which magnets are placed.

The illustrative magnetic drive system 300 shown in FIGS. 3A and 3B is not intended to suggest any limitation as to the scope of use or functionality of embodiments of the present disclosure. The illustrative magnetic drive system 300 also should not be interpreted as having any dependency or requirement related to any single component or combination of components illustrated therein. Additionally, various components depicted in FIGS. 3A and 3B may be, in embodiments, integrated with various ones of the other components depicted therein (and/or components not illustrated), all of which are considered to be within the ambit of the present disclosure.

Figure 4A:
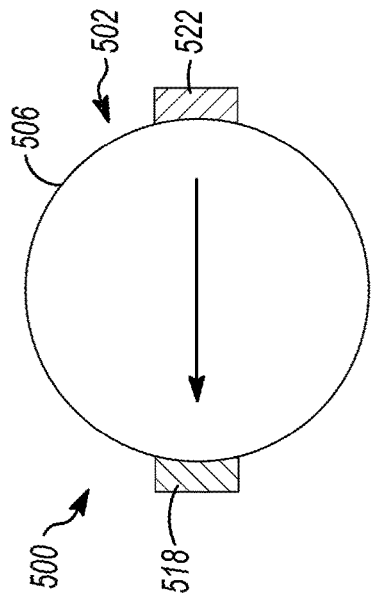
FIG. 4A depicts a top schematic view of an illustrative magnetic drive system, in accordance with embodiments of the subject matter disclosed herein.
Figure 4B:
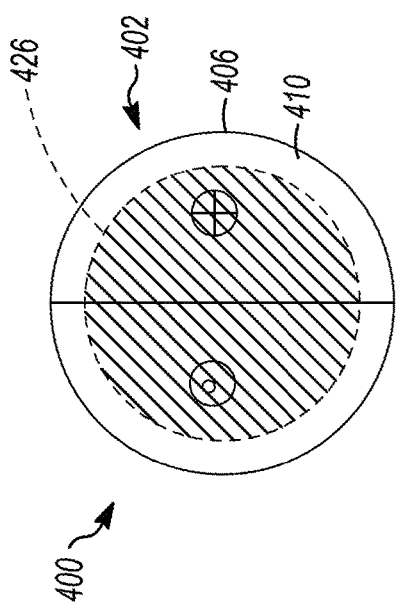
FIG. 4B depicts a schematic side view of the magnetic drive system depicted in FIG. 4A, in accordance with embodiments of the subject matter disclosed herein.

In embodiments, the flux enhancers may be provided at the ends of cylindrical bodies that are configured to have one or more pole pairs with only a little, or no, non-magnetic material provided between each adjacent section. FIG. 4A depicts a top schematic view of an illustrative magnetic drive system 400, in accordance with embodiments of the subject matter disclosed herein; and FIG. 4B depicts a schematic side view of the magnetic drive system 400 depicted in FIG. 4A, in accordance with embodiments of the subject matter disclosed herein. According to embodiments, the magnetic drive system 400, and/or any number of various components thereof, may be the same as, or similar to, corresponding components of the circulatory support device 100 depicted in FIG. 1.

As shown in FIGS. 4A and 4B, the magnetic drive system 400 includes a driven magnet assembly 402 configured to be driven by a driving magnet assembly 404. According to embodiments, each of the driven magnet assembly 402 and the driving magnet assembly 404 may include any number of pole pairs (e.g., 1, 2, 3, 4, 5, 6, 7, 8, 9, 10, etc.). The driven magnet assembly 402 includes a first cylindrical body 406 having a proximal end 408 and a distal end 410. Similarly, the driving magnet assembly 404 includes a second cylindrical body 412 having a proximal end 414 and a distal end 416.

As shown, the first cylindrical body 406 includes a first section 418 extending between the proximal and distal ends 408 and 410 and having a circular segment cross section, and a second section 420 extending between the proximal and distal ends 408 and 410 and having a circular segment cross section. As shown, the first section 418 may include a permanent magnet having a magnetic field that is directed in the proximal direction, while the second section 420 may include a permanent magnet having a magnetic field that is directed in the distal direction.

Similarly, the second cylindrical body 412 includes a first section 422 extending between the proximal and distal ends 414 and 416 and having a circular segment cross section, and a second section 424 extending between the proximal and distal ends 414 and 416 and having a circular segment cross section. As shown, the first section 422 may include a permanent magnet having a magnetic field that is directed in the proximal direction, while the second section 424 may include a permanent magnet having a magnetic field that is directed in the distal direction.

A first flux enhancer 426 is disposed on the distal end 410 of the first cylindrical body 406 and covers at least a portion of the distal end 410 of the first cylindrical body 406. Similarly, a second flux enhancer 428 may be disposed on the proximal end 414 of the second cylindrical body 412 and may cover at least a portion of the proximal end 414 of the second cylindrical body 412. The flux enhancers 426 and 428 may be, for example, discs made from soft magnetic material. The size (e.g., volume, length, and/or other dimensions) of the flux enhancers may be designed to maximize magnetic flux therethrough to maximize, optimize, or otherwise facilitate magnetic coupling between the driven magnet assembly 402 and the driving magnet assembly 404.

According to embodiments, as indicated above, the driven magnet assembly 402 and/or the driving magnet assembly 404 may include more than one pole pair. That is, for example, each cylindrical body may include a number of sections, each pair of sections having opposite magnetic poles. In embodiments, then, each section may have a cross-section that is a different shape than a circular segment, such as, for example, a pie-piece shape. In some embodiments, each section may be cylindrical. To facilitate manufacturing, in embodiments, a cylindrical body of a magnet assembly may be made from non-magnetic material and may include chambers defined therein into which magnets are placed.

The illustrative magnetic drive system 400 shown in FIGS. 4A and 4B is not intended to suggest any limitation as to the scope of use or functionality of embodiments of the present disclosure. The illustrative magnetic drive system 400 also should not be interpreted as having any dependency or requirement related to any single component or combination of components illustrated therein. Additionally, various components depicted in FIGS. 4A and 4B may be, in embodiments, integrated with various ones of the other components depicted therein (and/or components not illustrated), all of which are considered to be within the ambit of the present disclosure.

Figure 5A:
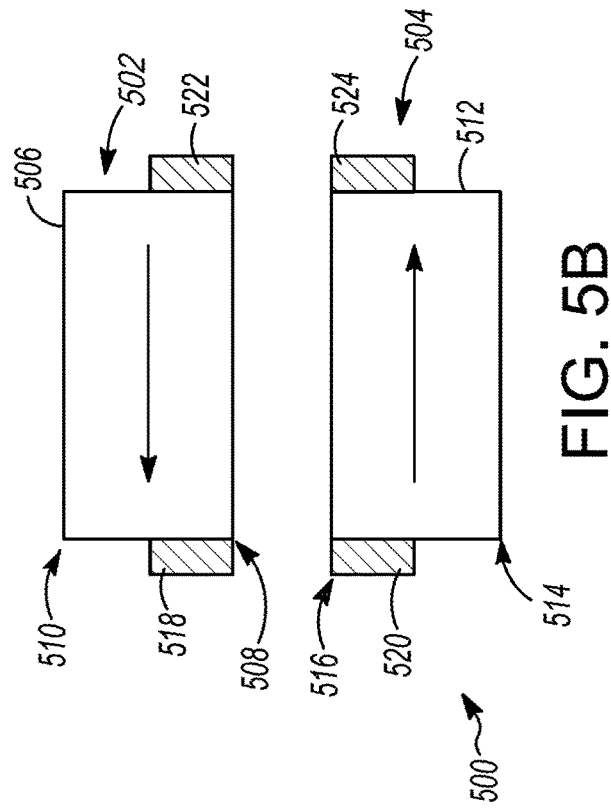
FIG. 5A depicts a top schematic view of an illustrative magnetic drive system, in accordance with embodiments of the subject matter disclosed herein.
Figure 5B:
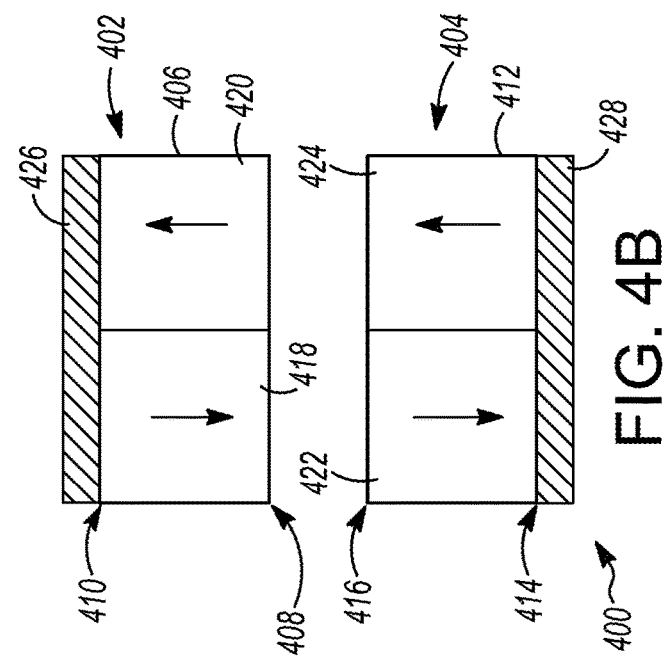
FIG. 5B depicts a schematic side view of the magnetic drive system depicted in FIG. 5A, in accordance with embodiments of the subject matter disclosed herein.

In embodiments, the flux enhancers may be, or include, features attached to the sides of the cylindrical bodies. FIG. 5A depicts a top schematic view of an illustrative magnetic drive system 500, in accordance with embodiments of the subject matter disclosed herein; and FIG. 5B depicts a schematic side view of the magnetic drive system 500 depicted in FIG. 5A, in accordance with embodiments of the subject matter disclosed herein. According to embodiments, the magnetic drive system 500, and/or any number of various components thereof, may be the same as, or similar to, corresponding components of the circulatory support device 100 depicted in FIG. 1.

As shown in FIGS. 5A and 5B, the magnetic drive system 500 includes a driven magnet assembly 502 configured to be driven by a driving magnet assembly 504. According to embodiments, each of the driven magnet assembly 502 and the driving magnet assembly 504 may include any number of pole pairs (e.g., 1, 2, 3, 4, 5, 6, 7, 8, 9, 10, etc.). In other embodiments, as shown in FIGS. 5A and 5B, each of the driven magnet assembly 502 and the driving magnet assembly 504 may include a single permanent magnet with a magnetic field aligned perpendicular to the drive shaft (not shown). The driven magnet assembly 502 includes a first cylindrical body 506 having a proximal end 508 and a distal end 510. Similarly, the driving magnet assembly 504 includes a second cylindrical body 512 having a proximal end 514 and a distal end 516.

The driven magnet assembly 502 includes a first flux enhancer 518 and the driving magnet assembly 504 includes a second, corresponding, flux enhancer 520. Similarly, the driven magnet assembly 502 further includes a third flux enhancer 522 and the driving magnet assembly 504 further includes a fourth flux enhancer 524. As shown, the first and third flux enhancers 518 and 522 are side irons disposed adjacent opposite magnetic poles on an outside of the first cylindrical body 506, and the second and fourth flux enhancers 520 and 524 are side irons disposed adjacent opposite magnetic poles on an outside of the second cylindrical body 512. As shown, the flux enhancers do not extend the entire axial length of the respective cylindrical bodies 506 and 512. The size (e.g., volume, length, and/or other dimensions) of the flux enhancers may be designed to maximize magnetic flux therethrough to maximize, optimize, or otherwise facilitate magnetic coupling between the driven magnet assembly 502 and the driving magnet assembly 504.

The illustrative magnetic drive system 500 shown in FIGS. 5A and 5B is not intended to suggest any limitation as to the scope of use or functionality of embodiments of the present disclosure. The illustrative magnetic drive system 500 also should not be interpreted as having any dependency or requirement related to any single component or combination of components illustrated therein. Additionally, various components depicted in FIGS. 5A and 5B may be, in embodiments, integrated with various ones of the other components depicted therein (and/or components not illustrated), all of which are considered to be within the ambit of the present disclosure.

In embodiments, the flux enhancers may include permanent magnets instead of soft magnetic material. FIG. 6A depicts a top schematic view of an illustrative magnetic drive system 600, in accordance with embodiments of the subject matter disclosed herein; and FIG. 6B depicts a schematic side view of the magnetic drive system 600 depicted in FIG. 6A, in accordance with embodiments of the subject matter disclosed herein. According to embodiments, the magnetic drive system 600, and/or any number of various components thereof, may be the same as, or similar to, corresponding components of the circulatory support device 100 depicted in FIG. 1.

As shown in FIGS. 6A and 6B, the magnetic drive system 600 includes a driven magnet assembly 602 configured to be driven by a driving magnet assembly 604. According to embodiments, each of the driven magnet assembly 602 and the driving magnet assembly 604 may include any number of pole pairs (e.g., 1, 2, 3, 4, 5, 6, 7, 8, 9, 10, etc.). The driven magnet assembly 602 includes a first cylindrical body 606 having a proximal end 608 and a distal end 610. Similarly, the driving magnet assembly 604 includes a second cylindrical body 612 having a proximal end 614 and a distal end 616. As shown in FIGS. 6A and 6B, each of the driven magnet assembly 602 and the driving magnet assembly 604 includes a Halbach array.

The first cylindrical body 606 includes a first section 618 extending between the proximal and distal ends 608 and 610 and having a circular segment cross section, a second section 620 extending between the proximal and distal ends 608 and 610 and having a circular segment cross section, and a third section 622 disposed between the first and second sections 618 and 620 and extending between the proximal and distal ends 608 and 610. As shown, the first section 618 may include a permanent magnet having a magnetic field that is directed in the proximal direction, while the second section 620 may include a permanent magnet having a magnetic field that is directed in the distal direction. The third section 622 may include a permanent magnet that has a magnetic field directed perpendicular to the magnetic fields of the first and second sections 618 and 620.

Similarly, the second cylindrical body 612 includes a first section 624 extending between the proximal and distal ends 614 and 616 and having a circular segment cross section, a second section 626 extending between the proximal and distal ends 614 and 616 and having a circular segment cross section, and a third section 628 disposed between the first and second sections 624 and 626 and extending between the proximal and distal ends 614 and 616. As shown, the first section 624 may include a permanent magnet having a magnetic field that is directed in the proximal direction, while the second section 626 may include a permanent magnet having a magnetic field that is directed in the distal direction. The third section 628 may include a permanent magnet that has a magnetic field directed perpendicular to the magnetic fields of the first and second sections 624 and 626.

The illustrative magnetic drive system 600 shown in FIGS. 6A and 6B is not intended to suggest any limitation as to the scope of use or functionality of embodiments of the present disclosure. The illustrative magnetic drive system 600 also should not be interpreted as having any dependency or requirement related to any single component or combination of components illustrated therein. Additionally, various components depicted in FIGS. 6A and 6B may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A magnetic drive system of a blood pump, the magnetic drive system comprising:
   an impeller;
   a drive shaft coupled to the impeller and configured to rotate with the impeller;
   a driven magnet assembly coupled to at least one of the drive shaft and the impeller; and
   a driving magnet assembly magnetically coupled to and thereby configured to drive the driven magnet assembly, wherein the driven magnet assembly including a first flux enhancer and the driving magnet assembly including a second flux enhancer, the first flux enhancer and the second flux enhancer comprising a soft magnetic material.

2. The magnetic drive system of claim 1, the driven magnet assembly comprising a first cylindrical body having a proximal end and a distal end; and the driving magnet assembly comprising a second cylindrical body having a proximal end and a distal end.

3. The magnetic drive system of claim 2, the first cylindrical body including a first section extending between the proximal and distal ends and having a circular segment cross section, a second section extending between the proximal and distal ends and having a circular segment cross section, and a third section disposed between the first and second sections and extending between the proximal and distal ends.

4. The magnetic drive system of claim 2, wherein the first flux enhancer is disposed on the distal end of the first cylindrical body and covers at least a portion of the distal end of the first cylindrical body.

5. The magnetic drive system of claim 3, wherein the third section of the first cylindrical body comprises:
   a first portion having a first end and a second end, wherein the first end is disposed at the distal end of the first cylindrical body, and wherein the first portion extends from the distal end to the second end; and
   a second portion having a first end and a second end, wherein the first end is disposed adjacent the second end of the first portion, and wherein the second portion extends from the first end to the proximal end of the first cylindrical body, wherein the first portion of the third section of the first cylindrical body comprises the first flux enhancer.

6. The magnetic drive system of claim 5, wherein the second portion of the third section of the first cylindrical body has an axial length that is approximately two times longer than an axial length of the first portion of the third section.

7. The magnetic drive system of claim 2, the second cylindrical body including a first section extending between the proximal and distal ends and having a circular segment cross section, a second section extending between the proximal and distal ends and having a circular segment cross section, and a third section disposed between the first and second sections and extending between the proximal and distal ends.

8. The magnetic drive system of claim 7, wherein the second flux enhancer is disposed on the proximal end of the second cylindrical body and covers at least a portion of the proximal end of the second cylindrical body.

9. The magnetic drive system of claim 7, wherein the third section of the second cylindrical body comprises:
   a first portion having a first end and a second end, wherein the first end is disposed at the proximal end of the second cylindrical body, and wherein the first portion extends from the proximal end to the second end; and
   a second portion having a first end and a second end, wherein the first end is disposed adjacent the second end of the first portion, and wherein the second portion extends from the first end to the distal end of the second cylindrical body,
   wherein the first portion of the third section of the second cylindrical body comprises the second flux enhancer.

10. The magnetic drive system of claim 2, the driven magnet assembly further comprising a third flux enhancer and the driving magnet assembly further comprising a fourth flux enhancer, wherein the first and third flux enhancers comprise sides irons disposed adjacent opposite magnetic poles on an outside of the first cylindrical body, and wherein the second and fourth flux enhancers comprise side irons disposed adjacent opposite magnetic poles on an outside of the second cylindrical body.

11. A magnetic drive system of a blood pump, the magnetic drive system comprising:
   an impeller;
   a drive shaft coupled to the impeller and configured to rotate with the impeller;
   a first bearing assembly disposed proximally from the impeller;
   a second bearing assembly disposed distally from the impeller;
   a driven magnet assembly coupled to at least one of the drive shaft and the impeller; and
   a driving magnet assembly configured to drive the driven magnet assembly, wherein at least one of the driven magnet assembly and the driving magnet assembly includes a flux enhancer, wherein at least one of the driven magnet assembly and the driving magnet assembly comprises two or more pole pairs.

12. A blood pump having a magnetic drive system, the magnetic drive system comprising:

an impeller;
a drive shaft coupled to the impeller and configured to rotate with the impeller;
a driven magnet assembly coupled to at least one of the drive shaft and the impeller; and
a driving magnet assembly coupled to a motor and configured to drive the driven magnet assembly, wherein the driven magnet assembly includes a first flux enhancer and the driving magnet assembly includes a second flux enhancer, the first flux enhancer and the second flux enhancer comprising a soft magnetic material, wherein the driven magnet assembly comprises a first cylindrical body having a proximal end and a distal end, the first cylindrical body including a first section extending between the proximal end and the distal end and having a circular segment cross section, a second section extending between the proximal end and the distal end and having a circular segment cross section, and a third section disposed between the first section and the second section and extending between the proximal end and the distal end, and wherein the driving magnet assembly comprises a second cylindrical body having a proximal end and a distal end.

13. The blood pump of claim 12, wherein the first flux enhancer is disposed on the distal end of the first cylindrical body and covers at least a portion of the distal end of the first cylindrical body.

* * * * *